United States Patent [19]

Bundy et al.

[11] 4,029,691

[45] June 14, 1977

[54] PROSTAGLANDIN $A_1$, ANALOGS

[75] Inventors: Gordon L. Bundy, Portage; John E. Pike, Kalamazoo, both of Mich.

[73] Assignee: The Upjohn Company, Kalamazoo, Mich.

[22] Filed: Dec. 24, 1975

[21] Appl. No.: 644,137

Related U.S. Application Data

[60] Continuation-in-part of Ser. No. 465,881, May 1, 1974, abandoned, which is a division of Ser. No. 288,848, Sept. 13, 1972, abandoned, which is a continuation of Ser. No. 72,105, Sept. 14, 1970, abandoned.

[52] U.S. Cl. .................. 260/468 D; 260/514 D; 424/305; 424/317
[51] Int. Cl.$^2$ .................................. C07C 177/00
[58] Field of Search ................... 260/514 D, 408 D

[56] References Cited

UNITED STATES PATENTS 3,729,502  4/1973  Beal et al. .................. 260/468

*Primary Examiner*—Robert Gerstl
*Attorney, Agent, or Firm*—Earl C. Spaeth

[57] ABSTRACT

Prostaglandin $A_1$ compounds with a methyl or an ethyl substituent at the C-15 position are disclosed. These are useful for the same pharmacological purposes as the unsubstituted prostaglandins A.

7 Claims, No Drawings

PROSTAGLANDIN A₁, ANALOGS

This application is a continuation-in-part of copending application Ser. No. 465,881, filed May 1, 1974, which is a division of copending application Ser. No. 288,848, filed Sept. 13, 1972, which is a continuation of copending application Ser. No. 72,105, filed Sept. 14, 1970, and all now abandoned.

DESCRIPTION OF THE INVENTION

This invention relates to novel compositions of matter, to novel methods for producing those, and to novel chemical intermediates useful in those processes. In particular, this invention relates to novel derivatives of prostanoic acid which has the following structure and atom numbering:

Various derivatives of parostanoic acid are known in the art. These are called prostaglandins. See, for example, Bergstrom et al., Pharmacol. Rev. 20, 1 (1968), and references cited therein. For example, prostaglandin $A_1$ ($PGA_1$) has the following structure:

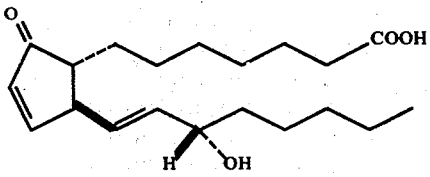

Prostaglandin $A_2$ ($PGA_2$) has the following structure:

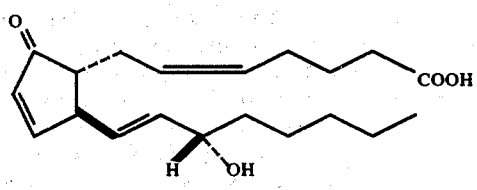

Prostaglandin $A_3$ ($PGA_3$) has the following structure:

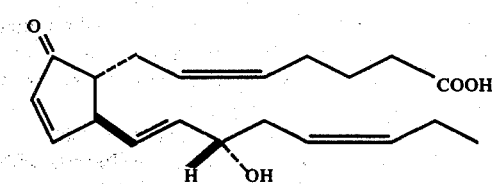

13,14-Dihydroprostaglandin $A_1$ (13,14-dihydro-$PGA_1$) has the following structure:

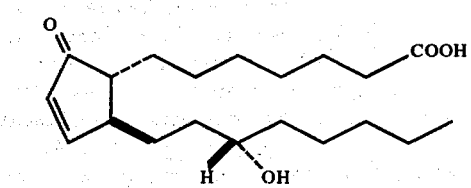

Prostaglandin $E_1$ ($PGE_1$) has the following structure:

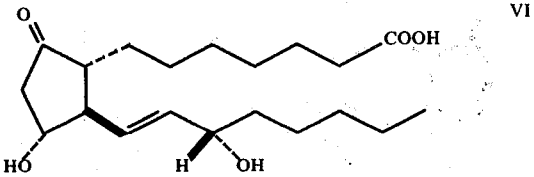

Prostaglandin $F_{1\alpha}$ ($PGF_{1\alpha}$) has the following structure:

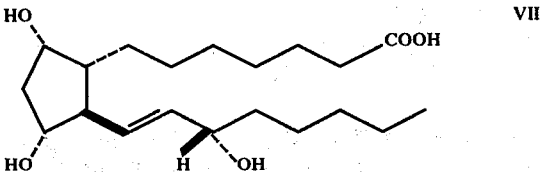

Prostaglandins E and F corresponding to $PGA_2$, $PGA_3$, and 13,14-dihydro-$PGA_1$ are also known.

In formulas II to VII, broken line attachments to the cyclopentane ring indicate substituents to alpha configuration, i.e., below the plane of the cyclopentane ring. Heavy solid line attachments to the cyclopentane ring indicate substituents in beta configuration, i.e., above the plane of the cyclopentane ring. The side-chain hydroxy at C-15 in formulas II to VII is in S configuration. See Nature, 212, 38 (1966) for discussion of the stereochemistry of ythe prostaglandins.

Molecules of the known prostaglandins each have several centers of asymmetry, and can exist in racemic (optically inactive) form and in either of the two enantiomeric (optically active) forms, i.e., the dextrorotatory and leverotatory forms. As drawn, formulas II to VII each represent the particular optically active form of the prostaglandin which is obtained from certain mammalian tissues, for example, sheep vesicular glands, swine lung, or human seminal plasma, or by carbonyl and/or double bond reduction or dehydration of a prostaglandin so obtained. See, for example, Bergstrom et al., cited above. The mirror image of each of formulas II to VII would represent the other enantiomer of that prostaglandin. The racemic form of a prostaglandin would contain equal numbers of both enantiomeric molecules, and one of formulas II to VII and the mirror image of that formula would both be needed to represent correctly the corresponding racemic prostaglandin. For convenience hereinafter, use of the terms $PGA_1$, $PGA_2$, $PGA_3$, 13,14-dihydro-$PGA_1$, $PGE_1$, $PGE_2$, $PGE_3$, and dihydro-$PGE_1$ will mean the optically active form of that prostaglandin with the same absolute configuration as $PGE_1$ obtained from mammalian tissues. When reference to the racemic form of one of those prostaglandins is intended, the word "racemic" will preceed the prostaglandin name, thus, racemic $PGA_1$ or racemic $PGE_1$.

Each of the novel prostanoic acid derivatives of this invention is encompassed by one of the following formulas or by the combination of that formula and its mirror image:

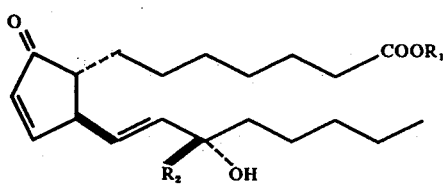

VIII

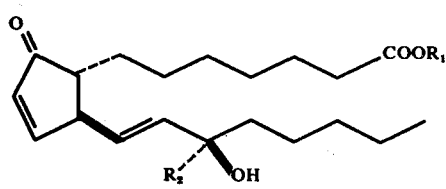

IX

In formulas VIII and IX, $R_1$ is hydrogen, alkyl of one to 8 carbon atoms, inclusive, or a pharmacologically acceptable cation, and $R_2$ is methyl or ethyl. In formula VIII the configuration of the hydroxy at C-15 is S as in the known prostaglandins of formulas II to VII. In formula IX the hydroxy at C-15 is in the unnatural R or epi configuration. See J. Chem. Education, 41, 116 (1964), for discussion of S and R configurations.

A significant characteristic of all of the known prostaglandins is the secondary hydroxy group at C-15, i.e., the atom grouping

Prostaglandins obtained from animal tissues always contain that atom grouping. In striking contrast, each of the novel prostanoic acid derivatives of this invention has a tertiary hydroxy group at C-15, i.e., the atom grouping

or the corresponding R or epi configuration grouping

wherein $R_2$ is methyl or ethyl. Thus, these novel prostanoic acid derivatives may conveniently be designated 15-methyl-prostaglandins $A_1$ or 15-ethylprostaglandins $A_1$, e.g., 15-methyl-PGA$_1$ or 15-ethyl15(R)-PGA$_2$.

As in the case of formulas II to VII, formulas VIII and IX are each intended to represent optically active prostanoic acid derivaties with the same absolute configuration as PGE$_1$ obtained from mammalian tissues. The novel prostanoic acid derivatives of this invention also include the corresponding racemic compounds. One of the formulas VIII or IX plus the mirror image of that formula are necessary in combination to describe a racemic compound. For convenience hereinafter, when the word "racemic" preceeds the name of one of the novel prostanoic acid derivatives of this invention, the intent is to designate a racemic compound represented by the combination of the appropriate formula VIII or IX and the mirror image of that formula. When the word "racemic" does not preceed the compound name, the intent is to designate an optically active compound represented only by the appropriate formula VII or IX and with the same absolute configuration as PGE$_1$ obtained from animal tissues.

PGA$_1$, PGA$_2$, PGA$_3$, and 13,14-dihydro-PGA$_1$, i.e., the compounds of formulas II, III, IV, and V, respectively, and their esters and pharmacologically acceptable salts are extremely potent in causing various biological responses. For that reason, these compounds are useful for pharmacological purposes. See, for example, Bergstrom et al., cited above, and reference cited therein. See also British specification Nos. 1,097,157 and 1,097,533.

For example, these known prostaglandins A are useful in mammals, including man and certain useful animals, e.g., dogs and pigs, to reduce and control excessive gastric secretion, thereby reducing or avoiding gastrointestinal ulcer formation, and accelerating the healing of such ulcers already present in the gastrointestinal tract. For this purpose, the compounds are injected or infused intravenously, subcutaneously, or intramuscularly in an infusion dose range about 0.1 μg. to about 500 μg. per kg. of body weight per minute, or in a total daily dose by injection or infusion in the range about 0.1 to about 20 mg. per kg. of body weight per day, the exact dose depending on the age, weight, and condition of the patient or animal, and on the frequency and route of administration.

Also, these known prostaglandins A are useful as hypotensive agents to reduce blood pressure in mammals, including man. For this purpose, the compounds are administered by intravenous infusion at the rate about 0.01 to about 50 μg. per kg. of body weight per minute, or in single or multiple doses of about 25 to 500 μg. of body weight total per day.

Also, these known prostaglandins A increase the flow of blood in the mammalian kidney, thereby increasing volume and electrolyte content of the urine. Therefore, these compounds are useful in managing cases of renal disfunction, especially those involving blockage of the renal vascular bed. Illustratively, the compounds are useful to alleviate and correct cases of edema resulting, for example, from massive surface burns, and in the management of shock. For these purposes, the compounds are preferably first administered by intravenous injection at a dose in the range 10 to 1000 μg. per kg. of body weight or by intravenous infusion at a dose in the range 0.1 to 20 μg. per kg. of body weight per minute until the desired effect is obtained. Subsequent doses are given by intraveneous, intramuscular, or subcutaneous injection or infusion in the range 0.05 to 2 mg. per kg. of body weight per day.

These known prostaglandins A are also useful in reducing the undesirable gastrointestinal effects resulting from systemic administration of anti-inflammatory prostaglandin synthetase inhibitors, and are used for that purpose by concomitant administration of the prostaglandin and the antiinflammatory prostaglandin synthetase inhibitor. See, for example, Partridge et al., U.S. Pat. No. 3,781,429, for a disclosure that the ulcerogenic effect induced by certain non-steroidal anti-inflammatory agents in rats is inhibited by concomitant oral administration of certain prostaglandins of the A$_1$ series, including PGA$_1$. Known prostaglandins of the A series are useful, for example, in reducing the undesirable gastrointestinal effects resulting from systemic administration of indomethacin, phenylbutazone, and aspirin. These are substances specifically mentioned in Partridge et al. as non-steroidal, antiinflammatory agents. These are also known to be prostaglandin synthetase inhibitors.

the anti-inflammatory synthetase inhibitor, for example, indomethacin, aspirin, or phenylbutazone is administered in any of the ways known in the art to alleviate an inflammatory condition, for example, in any dosage regimen and by any of the known routes of systemic administration.

The prostaglandin A is administered along with the antiinflammatory prostaglandin synthetase inhibitor either by the same route of administration or by a different route. For example, if the anti-inflammatory substance is being aministered orally, the prostaglandin is also administered orally or, alternatively, is administered rectally in the form of a suppository or, in the case of women, vaginally in the form of a suppository or a vaginal device for slow release, for example as described in U.S. Pat. No. 3,545,439. Alternatively, if the anti-inflammatory substance is being administered rectally, the prostaglandin is also administered rectally, the prostaglandin is also administered rectally, or, alternatively, orally or, in the case of women, vaginally. It is especially convenient when the administration route is to be the same for both anti-inflammatory substance and prostaglandin, to combine both into a single dosage form.

The dosage regimen for the prostaglandin in accord with this treatment will depend upon a variety of factors, includng the type, age, weight, sex and medical condition of the mammal, the nature and dosage regimen of the anitinflammatory synthetase inhibitor being adminnistered to the mammal, the sensitivity of the particular individual mammal to the particular synthetase inhibitor with regard to gastrointestinal effects, and the particular prostaglandin to be administered. For example, not every human in need of an anti-inflammatory substance experienced the same adverse gastrointenstinal effects when taking the substance. The gastrointestinal effects will frequently vary substantially in kind and degree. But it is within the skill of the attending physician or veterinarian to determine that administration of the antiinflammatory substance is causing undesirable gastrointestinal effects in the human or animal subject and to presecribe an effective amount of the prostaglandin to reduce and then substantially to eliminate those undesirable effects.

The novel 15-methyl and 15-ethyl prostaglandin $A_1$ analogs encompassed by formulas VIII and IX each cause the same biological responses described above for the known prostaglandins A, and each of these novel $PGA_1$ analogs is useful for the above-described pharmacological purposes, and is used for those purposes as described above. However, each of these 15-methyl and 15-ethyl prostaglandin $A_1$ analogs is surprisingly and unexpectedly more useful than the corresponding known prostaglandin for at least one of the pharmacological purposes described above because for that purpose the analog is more potent and has a substantially longer duration of activity. For that reason, fewer and smaller doses of these prostaglandin analogs are needed to attain the desired pharmacological results.

The novel prostaglandin $A_1$ analogs encompassed by formulas VIII and IX are used as described above in free acid form, in alkyl ester form, or in pharmacologically acceptable salt form. When the ester form is used, any alkyl ester can be used wherein the alkyl moiety contains one to 8 carbon atoms, inclusive, i.e., methyl, ethyl, propyl, butyl, pentyl, hexyl, heptyl, octyl, and isomeric forms thereof. However, it is preferred that the ester be alkyl of one to four carbon atoms, inclusive. Of those alkyl, methyl and ethyl are especially preferred for optimum absorption of the compound by the body or experimental animal system.

Pharmacologically acceptable salts of these prostaglandin analogs useful for the purposes described above are those with pharmacologically acceptable metal cations, ammonium, amine cations or quaternary ammonium cations.

Especially preferred metal cations are those derived from the alkali metals, e.g., lithium, sodium and potassium, and from the alkaline earth metals, e.g., magnesium and calcium, although cationic forms of other metals, e.g., aluminum, zinc, and iron, are within the scope of this invention.

Pharmacologically acceptable amine cations are those derived from primary, secondary, or tertiary amines. Examples of suitable amines are methylamine, dimethylamine, triemethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and like aliphatic, cycloaliphatic, and araliphatic amines containing up to and including about 18 carbon atoms, as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-a mino-2-ethyl-1,3-propanediol, 2-amino-2-methyl-1-propanol, tris(hydroxymethyl)aminomethane, N-phenylethanolamine, N-(p-tertamylphenyl)-diethanolamine, galactamine, N-methylglucamine, N-methylglucosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium, and the like.

As discussed above, the novel prostaglandin analogs are adminstered in various ways for various purposes, e.g., intravenously, intramuscularly, and subcutaneously.

For intravenous injection or infusion, sterile aqueous isotonic solutions are preferred. For that purpose, it is preferred because of increased water solubility to use the free acid form or the pharmacologically acceptable salt form. For subcutaneous or intramuscular injection, sterile solutions or suspensions of the acid, salt, or ester form in aqueous or non-aqueous media are used.

The novel 15-methyl and 15-ethyl prostaglandins $A_1$ of formulas VIII and IX wherein $R_1$ is hydrogen or alkyl of one to 8 carbon atoms, inclusive, ae prepared by the reactions defined in Chart A. in Chart A, $R_2$ is as defined above, and $R_3$ is hydrogen or alkyl of one to 8 carbon atoms, inclusive.

These reactions in Chart A are dehydrations. Any of the known substantially neutral dehydrating agents is used for these reactions. Preferred dehydratinhg agents are mixtures of at least an equivalent amount of a carbodiimide and a catalytic amount of a copper(II) salt. Expecially preferred are mixtures of at least an equivalent amount of dicyclohexylcarbodiimide and a catalytic amount of copper(II) chloride. An equivalent amount of a carbodiimide means one mole of the carbodiimide for each mole of the formula X or XII reactant. To ensure completeness of the reaction, it is advantageous to use an excess of the carbodiimide, i.e., 1.5 to 5 or even more equivalents of carbodiimide.

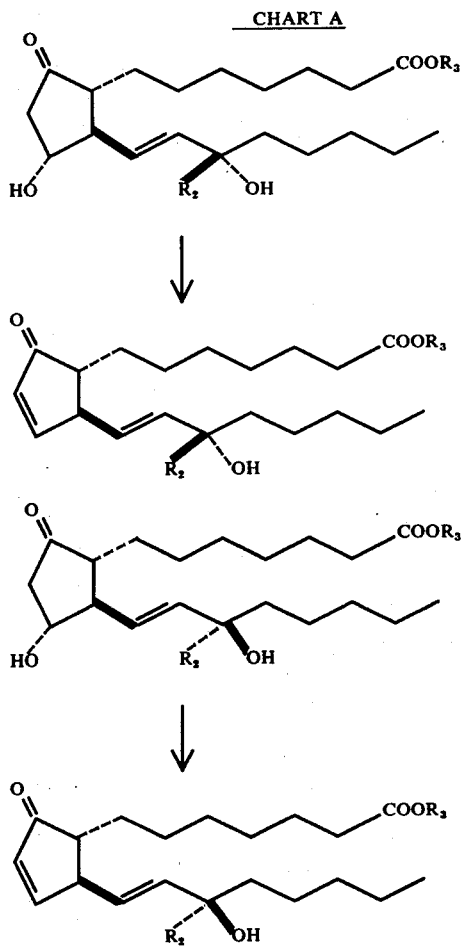

CHART A

The dehydration is advantageously carried out in the presence of an inert organic diluent which gives a homogeneous reaction mixture with respect to the formula X or XII reactant and the carbodiimide. Diethyl ether is a suitable diluent.

It is advantageous to carry out the dehydration in an atmosphere of an inert gas, e.g., nitrogen, helium, or argon.

The time required for the dehydration will depend in part on the reaction temperature. With the reaction temperature in the range 20° to 30° C., the dehydration usually takes place in about 40 to 60 hours.

The formula XI or XIII product is isolated by methods known in the art, e.g., filtration of the reaction mixture and evaporation of the filtrate. The product is then purified by methods known in the art, advantageously by chromatography on silica gel.

The formula X and XII reactants are prepared as described in U.S. Pat. No. 3,728,382, which is incorporated herein by reference.

When a formula XI or XIII product wherein $R_3$ is hydrogen is prepared as described above, and an alkyl ester of that acid is desired, esterification is advantageously accomplished by interaction of the acid with the appropriate diazohydrocarbon. For example, when diazomethane is used, the methyl esters ae produced. Similar use of diazoethane, diazobutane, and 1-diazo-2-ethylhexane, for example, gives the ethyl, butyl, and 2-ethylhexyl esters, respectively.

Esterification with diazohydrocarbons is carried out by mixing a solution of the diazohydrocarbon in a suitable inert solvent, preferably diethyl ether, with the acid reactant, advantageously in the same or a different inert diluent. After the esterification reaction is complete, the solvent is removed by evaporation, and the ester purified if desired by conventional methods, preferably by chromatography. It is preferred that contact of the acid reactants with the diazohydrocarbon be no longer than necessary to effect the desired esterification, preferably about one to about ten minutes, to avoid undesired molecular changes. Diazohydrocarbons are known in the art or can be prepared by methods known in the art. See, for example, Organic Reactions, John Wiley & Sons, Inc., New York, N.Y., Vol. 8, pp. 389–394 (1954).

An alternative method for esterification of carboxyl moiety of the formula XI or XIII acid comprises transformation of said acid to the corresponding silver salt, followed by interaction of that salt with an alkyl iodide. Examples of suitable iodides are methyl iodide, ethyl iodide, butyl iodide, isobutyl iodide, tert-butyl iodide, and the like. The silver salts are prepared by conventional methods, for example, by dissolving the acid in cold dilute aqueous ammonia, evaporating the excess ammonia at reduced pressure, and then adding the stoichiometric amount of silver nitrate.

The novel formula VIII or IX acids ($R_1$ is hydrogen) are transformed to pharmacologically acceptable salts by neutralization with appropriate amounts of the corresponding inorganic or organic base, examples of which correspond to the cations and amines listed above. These transformations are carried out by a variety of procedures known in the art to be generally useful for the preparation of inorganic, i.e., metal or ammonium, salts amine acid addition salts, and quaternary ammonium salts. The choice of procedure depends in part upon the solubility characteristics of the particular salt to be prepared. In the case of the inorganic salts, it is usually suitable to dissolve the acid in water containing the stoichiometric amount of a hydroxide carbonate, or bicarbonate corresponding to the inorganic salt desired. For example, such use of sodium hydroxide, sodium carbonate, or sodium bicarbonate gives a solution of the sodium salt of the prostanoic acid derivative. Evaporation of the water or addition of a water-miscible solvent of moderate polarity, for example, a lower alkanol or a lower alkanone, gives the solid inorganic salt if that form is desired.

To produce an amine salt, the acid is dissolved in a suitable solvent of either moderate or low polarity. Example of the former are ethanol, acetone, and ethyl acetate. Examples of the latter are diethyl ether and benzene. At least a stoichiometric amount of the amine corresponding to the desired cation is then added to that solution. If the resulting salt does not precipitate, it is ususally obtained in solid form by addition of a miscible diluent of low polarity or by evaporation. If the amine is relatively volatile, any excess can easily be removed by evaporation. It it preferred to use stoichiometric amounts of the less volatile amines.

Salts wherein the cation is quaternary ammonium are produced by mixing the acid with the stoichiometric amount of the corresponding quarternary ammonium hydroxide in water solution, followed by evaporation of the water.

The invention can be more fully understood by the following examples.

EXAMPLE 1

15-Methyl-PGA$_1$ Methyl Ester.

A mixture of 15-methyl- PGE$_1$ methyl ester (6 mg.), dicyclohexylcarbodiimide (20 mg.), copper(II) chloride dihydrate (2 mg.), and diethyl ether (2 ml.) is stirred under nitrogen at 25° C. for 16 hours. Then, additional dicyclohexylcarbodiimide (20 mg.) is added, and the mixture is stirred an additional 32 hours at 25° C. under nitrogen. The resulting mixture is filtered, and the filtrate is evaporated under reduced pressure. The residue is chromatographed by preparative thin layer chromatography with the A-IX system to give 15-methyl-PGA$_1$ methyl ester.

EXAMPLE 2

15-Methyl-PGA$_1$.

A mixture of 15-methyl-PGE$_1$ (1.00 g.), dicyclohexylcarbodiimide (3.00 g.), copper(II) chloride (300 mg.), and diethyl ether (300 ml.) is stirred at 25° C. under nitrogen for 24 hours. Then, additional dicyclohexylcarbodiimide (3.00 g.) is added, and the mixture is stirred an additional 24 hours at 25° C. under nitrogen. The resulting mixture is filtered, and the filtrate is evaporated under reduced pressure. The residue is chromatographed on 300 g. of silica gel, eluting with 2 l. of a gradient of 25–100% ethyl acetate in Skellysolve B ( a mixture of isomeric hexanes). The eluate fractions containing the desired product as shown by TLC (A-IX) are combined and evaporated under reduced pressure to give 15-methyl-PGA$_1$.

Following the procedure of Example 2, 15-ethyl-PGE$_1$ is dehydrated to give 15-ethyl-PGA$_1$. Also following the procedure of Example 2, the racemic forms of 15-methyl-PGE$_1$ and 15-ethyl-PGE$_1$ are dehydrated to give the corresponding racemic forms of 15-methyl-PGA$_1$ and 15-ethyl-PGA$_1$, respectively.

Also following the procedure of Example 2, 15-methyl15(R)-PGE$_1$ and 15-ethyl-15(R)-PGE$_1$ and the racemic forms of each of those are each dehydrated to the corresponding optically active or racemic form of the 15-methyl-15(R) or 15-ethyl-15(R) prostaglandin A$_1$.

Also following the procedure of Example 2, the methyl, ethyl, tert-butyl, and 2-ethylhexyl esters of 15-methyl-PGE$_1$, 15-methyl-15(R)-PGE$_1$, 15-ethyl-PGE$_1$, and 15-ethyl-15(R)-PGE$_1$, and the racemic form of each of those are each dehydrated to the corresponding 15-methyl or 15-ethyl prostaglandin A$_1$ ester.

We claim:

1. An optically active compound of the formula:

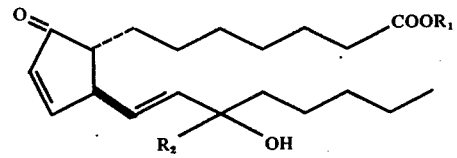

or a racemic compound of that formula and the mirror image thereof, wherein R$_1$ is hydrogen, alkyl of one to 8 carbon atoms, or a pharmacologically acceptable cation, wherein R$_2$ is methyl or ethyl, and wherein the side-chain hydroxy is in S or R configuration.

2. An optically active compound of the formula:

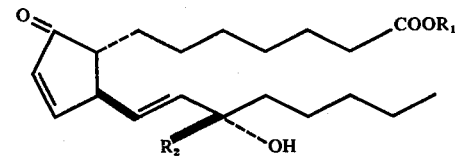

or a racemic compound of that formula and the mirror image thereof, wherein R$_1$ is hydrogen, alkyl of one to 8 carbon atoms, or a pharmacologically acceptable cation, and wherein R$_2$ is methyl or ethyl.

3. An optically active compound of the formula:

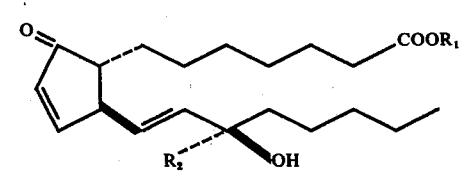

or a racemic compound of that formula and the mirror image thereof, wherein R$_1$ is hydrogen, alkyl of one to 8 carbon atoms, or a pharmacologically acceptable cation, and wherein R$_2$ is methyl or ethyl.

4. 15-Methyl-PGA$_1$, an optically active compound according to claim 2 wherein R$_1$ is hydrogen and R$_2$ is methyl.

5. 15-Methyl-PGA$_1$ methyl ester, an optically active compound according to claim 2 wherein R$_1$ and R$_2$ are both methyl.

6. 15-Methyl-15(R)-PGA$_1$, an optically active compound according to claim 3 wherein R$_1$ is hydrogen and R$_2$ is methyl.

7. 15-Methyl-15(R)-PGA$_1$ methyl ester, an optically active compound according to claim 3 wherein R$_1$ and R$_2$ are both methyl.

* * * * *